United States Patent
Plans et al.

(10) Patent No.: US 10,459,972 B2
(45) Date of Patent: Oct. 29, 2019

(54) BIOMETRIC-MUSIC INTERACTION METHODS AND SYSTEMS

(71) Applicant: BIOBEATS GROUP LTD, London OT (GB)

(72) Inventors: David Plans, Woking (GB); Davide Morelli, Leghorn (IT); Gabriele Cocco, Pisa (IT); Nadeem Kassam, Vancouver (CA)

(73) Assignee: BIOBEATS GROUP LTD, London (GB)

( * ) Notice: Subject to any disclaimer, the term of this patent is extended or adjusted under 35 U.S.C. 154(b) by 0 days.

(21) Appl. No.: 14/265,261

(22) Filed: Apr. 29, 2014

(65) Prior Publication Data
US 2015/0093729 A1    Apr. 2, 2015

Related U.S. Application Data (63) Continuation-in-part of application No. 14/021,862, filed on Sep. 9, 2013, now Pat. No. 9,330,680.
(Continued)

(51) Int. Cl.
| | |
|---|---|
| G09B 5/00 | (2006.01) |
| G09B 19/00 | (2006.01) |
| G06F 16/683 | (2019.01) |
| A61B 5/0205 | (2006.01) |
| A61B 5/0402 | (2006.01) |
| A61B 5/0476 | (2006.01) |

(Continued)

(52) U.S. Cl.
CPC ............. *G06F 16/683* (2019.01); *A61B 5/01* (2013.01); *A61B 5/02055* (2013.01); *A61B 5/0402* (2013.01); *A61B 5/0476* (2013.01); *A61B 5/11* (2013.01); *A61B 5/14551* (2013.01); *G09B 5/00* (2013.01); *G09B 19/00* (2013.01); *A61B 5/02416* (2013.01); *A61B 5/0816* (2013.01)

(58) Field of Classification Search
CPC .................................. G09B 5/00; G09B 19/00
See application file for complete search history.

(56) References Cited

U.S. PATENT DOCUMENTS

| | | |
|---|---|---|
| 4,883,067 A | 11/1989 | Knispel et al. |
| 7,177,672 B2 | 2/2007 | Nissila |

(Continued)

FOREIGN PATENT DOCUMENTS

| | | |
|---|---|---|
| WO | WO 2013/166341 A1 | 11/2013 |
| WO | WO 2013/170032 A2 | 11/2013 |

OTHER PUBLICATIONS

ACPRC. Leaflet No. GL-05. "The Active Cycle of Breathing Techniques". Published 2011.*

(Continued)

*Primary Examiner* — Robert J Utama
(74) *Attorney, Agent, or Firm* — Innovation Capital Law Group, LLP; Vic Lin (57) ABSTRACT

A system and method for the automatic, procedural generation of musical content in relation to biometric data. The systems and methods use a user's device, such as a cell phone to capture image data of a body part, and derive a biometric signal from the image data. The biometric signal includes biometric parameters, which are used by a music generation engine to generate music. The music generation can also be based on user-specific data and quality data related to the biometric detection process.

18 Claims, 5 Drawing Sheets

Related U.S. Application Data (60) Provisional application No. 61/697,938, filed on Sep. 7, 2012, provisional application No. 61/817,708, filed on Apr. 30, 2013, provisional application No. 61/818,993, filed on May 3, 2013, provisional application No. 61/819,785, filed on May 6, 2013.

(51) Int. Cl.
*A61B 5/01* (2006.01)
*A61B 5/1455* (2006.01)
*A61B 5/11* (2006.01)
*A61B 5/024* (2006.01)
*A61B 5/08* (2006.01)

(56) References Cited

U.S. PATENT DOCUMENTS

| | | | |
|---|---|---|---|
| 7,207,935 | B1 | 4/2007 | Lipo |
| 7,606,790 | B2 | 10/2009 | Levy |
| 8,055,667 | B2 | 11/2011 | Levy |
| 8,183,451 | B1 | 5/2012 | Panatiotis |
| 2004/0044897 | A1 | 3/2004 | Lim |
| 2004/0077934 | A1* | 4/2004 | Massad ............... A61B 5/1135 600/300 |
| 2004/0243567 | A1 | 12/2004 | Levy |
| 2008/0095410 | A1 | 4/2008 | Shalev et al. |
| 2008/0257133 | A1 | 10/2008 | Sasaki et al. |
| 2008/0275915 | A1 | 11/2008 | Dunbar et al. |
| 2009/0226071 | A1 | 9/2009 | Schuler et al. |
| 2010/0037753 | A1 | 2/2010 | Wagner |
| 2010/0161654 | A1 | 6/2010 | Levy |
| 2011/0251493 | A1* | 10/2011 | Poh .................. G06F 19/00 600/477 |
| 2012/0225412 | A1 | 9/2012 | Wagner |
| 2013/0047229 | A1 | 2/2013 | Hoefel et al. |

OTHER PUBLICATIONS

ChicagoTribune. 'Overwhelmed? Overbooked? Overholidayed? Take a Breather'. Published Nov. 30, 2011. Acquired from <http://articles.chicagotribune.com/2011-11-30/health/sc-health-1130-mental-stress-apps-20111130_1_android-app-heart-rate>.*

Abramson, Paul MD. 'An app that makes it easy to learn and implement breathing exercises (pranayama)'. Published Nov. 13, 2011. Acquired from <http://quantdoctor.com/2011/11/13/app-to-learn-breathing-pranayama/>.*

International Search Report dated Oct. 9, 2015, regarding PCT/US2015/028313.

Casal, D.P.: "*Remember the Future: Genetic Co-Evolution and MPEG7 Matching in the Creation of Artificial Music Improvisors*", Mar. 2008.

Plans, D. et al.: "*Experience-Driven Procedural Music Generation for Games*", IEEE Transaction on Computational Intelligence and Al in Games, Special Issue: Computational Aesthetics in Games, Jun. 2012.

Casal, D.P. et al.: "*Remembering the future: towards an application of genetic co-evolution in music improvisation*"; MusicAL Workshop, European Conference on Artificial Life, Lisboa, Portuga, 2007, pp. 1-12.

\* cited by examiner

BIOMETRIC-MUSIC INTERACTION METHODS AND SYSTEMS

CROSS REFERENCE TO RELATED APPLICATION(S)

This application is a continuation-in-part application of U.S. application Ser. No. 14/021,862, filed Sep. 9, 2013, currently pending; which claims the benefit under 35 USC § 119(e) to U.S. Provisional Application 61/697,938, filed on Sep. 7, 2012; this application also claims the benefit under 35 USC § 119(e) to U.S. Provisional Application 61/817,708, filed on Apr. 30, 2013; U.S. Provisional Application 61/818,993, filed on Mar. 3, 2013; and U.S. Provisional Application 61/819,785, filed on Mar. 6, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

BACKGROUND OF THE INVENTION

Field of the Invention

The field of invention includes technologies relating to the procedural generation of a computerized response based on user biometric measurements.

Background Information

The following description includes information that may be useful in understanding the present invention. It is not an admission that any of the information provided herein is prior art or relevant to the presently claimed invention, or that any publication specifically or implicitly referenced is prior art.

Chronic stress and its effects on cardiovascular health is an area of a person's health that is frequently neglected or overlooked. Factors such as sedentary lifestyles, stressful jobs and unhealthy eating habits increase the risk that a person will have poor cardiovascular health and/or a coronary event, the person often only finding out about it when it is too late. Existing systems and methods for the self-monitoring of cardiovascular health have attempted to engage users by providing using a person's health information to create music or sounds. However, these systems and methods typically require medical knowledge to understand cardiovascular health information, highly technical, specialized monitoring devices (which themselves require specialized knowledge for proper use) or both. As such, these existing systems and methods of monitoring cardiovascular health remain too difficult, costly and/or cumbersome for the average consumer to use.

Others have put forth efforts towards user-friendly cardiovascular health applications by applying biometric information to music:

US patent application publication 2004/0077934 to Massad titled "Interventive-Diagnostic Device", published Apr. 22, 2004, discusses the use of biometric information to generate music. However, the system in Massad requires specialized sensors to gather the biometric data needed for the music generation, and the complexity of the system requires training or specialized education for application, such as from a physician. Additionally, Massad fails to incorporate forecasted events into the music generation.

US patent application publication 2008/0257133 to Sasaki, et al titled "Apparatus and Method for Automatically Creating Music Piece Data", published Oct. 23, 2008, discusses using a user's heart rate as a condition for creating a music piece data file, so as to control the tempo of the music. However, the system discussed in Sasaki requires a specialized sensor to detect the heart rate of the wearer. Additionally, the system in Sasaki discloses using only a heart rate to determine tempo, upon which a template is selected to generate the music. No other measured biometric characteristics are used to affect the music generation. Likewise, the system in Sasaki lacks the incorporation of biometric forecasting into the music generation process.

U.S. Pat. No. 7,177,672 to Nissila titled "Coding Heart Rate Information", issued Feb. 13, 2007, discusses generating music based on a measured heart rate. Sound elements are selected for music production based on the heart rate level, such as by a tempo associated with the heart rate level. Nissila does not discuss incorporating other biometric measurements or biometric predictions into the music generation process, and requires specialized equipment for the detection of heart beats.

US patent application publication 2009/0226071 to Schuler, et al titled "Method and Apparatus to Facilitate Using Visible Light Images to Determine a Heart Rate", published Sep. 10, 2009, discusses determining a heart beat from images, such as images having RGB color components. Schuler does not discuss using the determined heart beat to generate music or other enhanced content for a user. Additionally, Schuler does not discuss a user-friendly system that assists the user in the proper use of the system by using sonic or visual feedback.

US patent application publication 2011/0251493 to Poh, et al titled "Method and System for Measurement of Physiological Parameters", published Oct. 13, 2011, discusses using RGB image data to measure physiological parameters such as heart rate, respiratory rate, and heart rate variability. Poh does not discuss using the physiological data for any kind musical content generation.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need for user-friendly systems and methods that allow a user to derive insight into their stress and cardiovascular health in a comprehensible way by being engaging, easy to use and understand, without the need for additional complicated and/or expensive equipment. Additionally, there is a need for user-friendly systems and methods that allow for biometric data to be collected and aggregated, for example from multiple individuals simultaneously to understand the larger, epidemiology-level insights in cardiovascular health that can spot trends, and use the larger body of data to refine algorithms that look for significant changes in the person's data at the individual level. Further, there is a need for user-friendly systems and methods that allow for not only collection of biometric data (e.g., from using cell phone hardware as a photoplethysmograph), but also use of such data to construct one or more content lists (e.g., music play lists, videos, etc.) that can be curated to the state. Even further, there is a need for user-friendly systems and methods that allow cross-modality feedback (e.g., musical sonification, visual stimuli, etc.) from biometric data to generate therapeutic experiences for a user, such as guided breathing interventions that are directed towards lowering blood pressure, implementing such as Herbert Benson's relaxation response from controlled breathing (Herbert Benson, M. D., and Miriam Z. Klipper. *The relaxation response*. Harper Collins, New York, 1992).

SUMMARY OF THE INVENTION

The inventive subject matter provides apparatus, systems and methods to sonify biometric data along by incorporating unique user data and quality data such that the generated music output is interesting and informative to the user, and that assists the user with the use of the system to maximize its effectiveness.

The system includes an image sensor, such as a camera on a computing device, that the user can use to capture image data of a part of the body. The image data can be video data or a plurality of photos taken sequentially. The image sensor can also include a flash.

The system can also include a biometric detection engine communicatively coupled with the image sensor, and a music generation engine communicatively coupled to the biometric detection engine. Each of the biometric detection engine and the music generation engine can be computer-readable instructions stored on non-transitory memory (RAM, flash, ROM, hard drive, solid state, drive, optical media, etc.), coupled to one or more processors, where the instructions are executed by one or more processors to carry out various functions associated with the inventive subject matter. One or both of the biometric detection engine and the music generation engine can alternatively be a dedicated hardware device, such as a processor, specially programmed to carry out the functions associated with the inventive subject matter. One or both of the biometric detection engine and the music generation engine can include interfaces, such as communication or device interfaces, that can communicatively couple with separate devices, such as other computing devices, peripheral devices, etc.

The image sensor, biometric detection engine and music generation engine can be contained within a single device, such as a cellular phone that includes a camera, or other computing devices that include a suitable image sensor. Alternatively, the image sensor, biometric detection engine and music generation engine can each be contained within separate computing devices, communicatively connected via a network.

The biometric detection engine uses the captured image data derive a biometric signal and extract one or more biometric parameters associated with the signal. For example, the biometric detection engine can derive a periodic biometric signal and extract a heart rate, a percentage of oxygen in the user's blood, a temperature, an electrical signal (e.g., EKG, EEG, etc.), or other biometric parameter. The biometric detection engine can be configured to derive the biometric signal based on the RGB values of the received images.

The biometric parameters can then be used by the music generation engine to create one or more music signals, which can then be transmitted to a media player. The media player presents the music signal as music reflecting a biometric state of the user. The music signals can be generated by using music features associated with the derived biometric parameters.

In another aspect of the inventive subject matter, the image data captured by the image sensor can be separated into red, green and blue images. Each of the red, green and blue images can be weighted according to the strength of detection of the biometric signal. The weight proportion or other aspect of the analysis can then be used as an additional parameter used in the music generation process.

In a further aspect of the inventive subject matter, the optimal weighted proportion between the red, green and blue images can be stored for an individual user, allowing for an optimized detection configuration for an individual's unique skin. This allows the system to optimize the detection of biometrics for an individual's skin properties (e.g., tone, color, pigmentation, etc.). The weighted proportion can be tailored to account for variances in an individual's skin properties (e.g., a person's skin being more tan in the summer than winter, tan lines, differences in color between a person's skin being cold versus warm, etc.).

In another aspect of the inventive subject matter, a user can have one or more associated user configurations corresponding to a collection of image capture settings related to the image sensor (e.g., aperture settings, exposure settings, white balancing, etc.). The user configurations can be optimized for a particular user's skin characteristics (e.g., color, pigmentation, tone, presence of hair, scarring, etc.). A user can have multiple user configurations, to account for differences in skin from one body part to the next.

A user's profile can be used to store all of the information relevant to a particular user. The user's profile can include user-specific data related to the image capture and detection analysis, such as optimized detection configurations, RGB optimized weight values, user configurations related to image capture settings, etc. The system can include a user database to store the user profiles for each user.

In another aspect of the inventive subject matter, the music signal can be modified based on the quality of the images obtained via the camera. Accordingly, if the images are of low quality for the purposes of biometric detection, the music generated can be modified to alert the user to improve the quality of gathered images. The modifications can be perceived by the user as a degradation of the generated music signal, which can be used to guide the user in improving the image detection.

In another aspect of the inventive subject matter, long-term statistical health predictions (e.g., the onset of atherosclerosis, hypertension, dangerous levels of stress, etc.) can be made based on the gathered biometric information. The predictions can be incorporated into the music generation to reflect concerns such as the immediacy of the prediction, the severity of the condition predicted, the likelihood of the prediction, and the overall danger to the user's cardiovascular health.

The inventive subject matter provides apparatus, systems and methods in which a biometric processing system can aggregate biometric data across individuals within a crowd, an audience of a live performance for example, and generate a media presentation based on the aggregated biometric data. One aspect of the inventive subject matter includes a biometric processing system that includes a biometric interface and a processing engine. Biometric sensor interfaces, the audiences' cell phones for example, are configured to acquire biometric data sets from individual members of the crowd. Each biometric data set can be considered a digital object representative of the corresponding individual's biometric data (e.g., breath rate, heart rate, stress level, movement, blood pressure, etc.). The biometric processing engine, possibly disposed on cell phone or within a server, uses the biometric interface to obtain and process the biometric data sets. The biometric processing engine derives a group biometric state as function of the biometric data sets where the group biometric state is considered to reflect the state of the crowd. For example, the group biometric state can include average biometrics (e.g., average heart rate, average breath rate, average movement, etc.) or other statistical information. Based on the group biometric state; possibly based on attributes, statistical values, measures, trends, or other features, the processing engine compiles content into a media presentation. The engine further configures an output device to render the media presentation. The media presentation can be rendered for the crowd, an individual, a manager, a performer, a venue owner, or other stakeholder.

In another aspect, the inventive subject matter provides apparatus, systems and methods in which a biometric processing system can aggregate biometric data across individuals within a crowd, an audience of a live performance for example, and generate a media presentation based on the aggregated biometric data.

One aspect of the inventive subject matter includes a biometric processing system that includes a biometric interface and a processing engine. Biometric sensor interfaces, the audiences' cell phones for example, are configured to acquire biometric data sets from individual members of the crowd. Each biometric data set can be considered a digital object representative of the corresponding individual's biometric data (e.g., breath rate, heart rate, stress level, movement, blood pressure, etc.). The biometric processing engine, possibly disposed on cell phone or within a server, uses the biometric interface to obtain and process the biometric data sets. The biometric processing engine derives a group biometric state as function of the biometric data sets where the group biometric state is considered to reflect the state of the crowd. For example, the group biometric state can include average biometrics (e.g., average heart rate, average breath rate, average movement, etc.) or other statistical information. Based on the group biometric state; possibly based on attributes, statistical values, measures, trends, or other features, the processing engine compiles content into a media presentation. The engine further configures an output device to render the media presentation. The media presentation can be rendered for the crowd, an individual, a manager, a performer, a venue owner, or other stakeholder.

In another aspect, the inventive subject matter provides apparatus, systems and methods in which a computing device can operate as a content management engine to generate playlists, or other types of content listings, based on biometric data.

One aspect of the inventive subject matter includes configuring a mobile device to operate as a content management, such as by an application. The content management engine acquires biometric data from the device, possibly via one or more sensors (e.g., camera, accelerometers, microphone, local sensors, remote sensors, personal area sensors, medical sensors, etc.). The engine further derives a bio-state of an entity (e.g., user, human, animal, etc.) as a function of the biometric data. For example, the bio-state could include a psychological state, perhaps including stress levels, physiological state, or other bio-state. Based on the bio-state, the engine generates a content lists (e.g., music playlist) where the content referenced by the content lists can augment, enhance, diminish, or otherwise engage with the bio-state. The content management engine can further configure the mobile device to render the content referenced by the content list.

In yet another aspect, the inventive subject matter provides apparatus, systems and methods in which one or more devices are able to detect biometrics and to construct a therapy regimen, possibly including a multimodal therapy.

One aspect of the inventive subject matter includes a system including a biosensor interface and a therapy engine. The biosensor interface can take on many different forms including a smart phone, medical device, or other computing device configured or programmed to acquire biometric data. For example, a camera on a cell phone can capture image data of a person's flesh, which can then be used to determine heart beat, pulse oximetry or other types of biometric data. The therapy engine, possibly comprising a cell phone or remote server, obtains the biometric data via the biosensor interface. The engine can further construct a digital therapy regiment as a function of the biometric data. In some embodiments, the biometric data can be mapped to one or more types of therapy, perhaps based on a therapy template. The therapy regimen can comprise instructions that configure a device to render the therapy according to rendering instructions. The rendering instructions can cause the device to render a multimodal therapy having audio, visual, haptic, kinesthetic, or other forms of data.

Various objects, features, aspects and advantages of the inventive subject matter will become more apparent from the following detailed description of preferred embodiments, along with the accompanying drawing figures in which like numerals represent like components.

DETAILED DESCRIPTION OF THE INVENTION

It should be noted that while the following description is drawn to a computer/server based biometric data processing systems, various alternative configurations are also deemed suitable and may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including generating one or more music signals that configure a media player to present audio music.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. The terms "coupled to" and "coupled with" are also used euphemistically to mean "communicatively coupled with" where two or more networked devices are able to send or receive data over a network.

The disclosed systems and methods relate to sonification of data, and specifically, to a system and method for the musical sonification of a stream of biometric data (e.g., pulse (systolic and diastolic peak detection) and heart rate variability (the variation in the time interval between heart beats), personalization data and quality data. In embodiments, the systems and methods use the hardware of a user's device cell phone hardware and computing functions to construct a software photoplethysmograph (a pulse oximeter), using the device's camera, flash, and engines, modules and methods described below.

Figure 1:
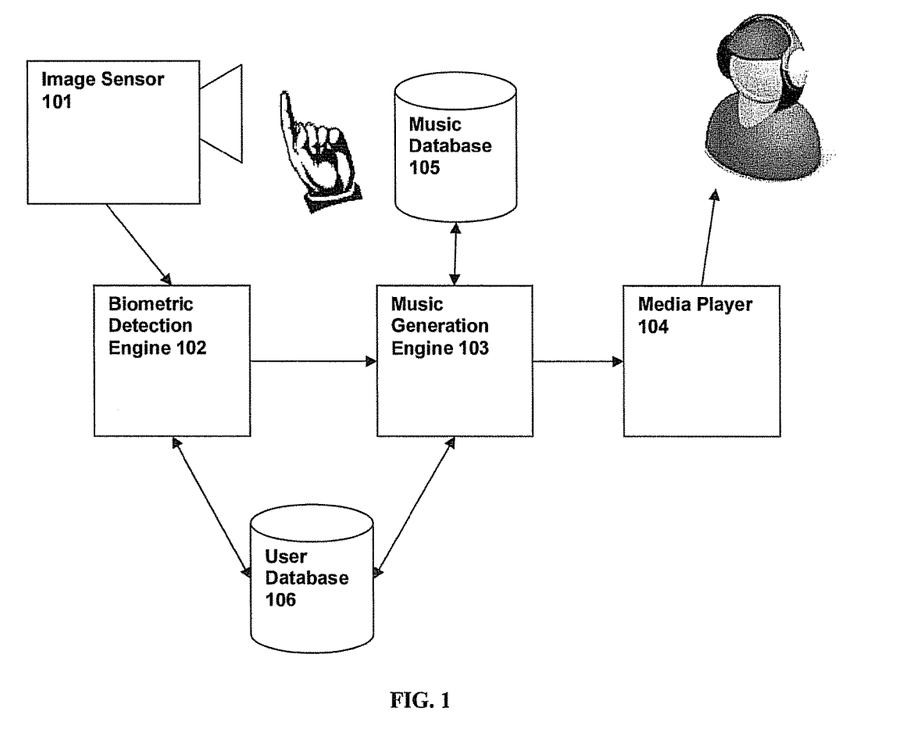
FIG. 1 is an overview of a sample implementation of the system and methods of the inventive subject matter.

As shown in FIG. 1, image sensor 101 can be used to take an image of a part of the user's body, preferably a body part having exposed skin (i.e., visible to the image sensor 101. The image sensor 101 can be a digital camera suitable for capturing image data, such as the camera on a user's cellular phone. For example, the user can place their finger in front of the phone's camera. The user can be encouraged or instructed, via visual or audio instructions presented through the cell phone, to take image data of a specific part of the body that maximizes the likelihood of detection, such as a part of the body that is easy for the user to reliably capture with the camera or a part of the body having major blood vessels. The cellular phone's flash can be employed to enhance the lighting on the user's body part, such as to compensate for poor environmental image capture conditions.

The image data captured by the image sensor 101 is preferably a video, but can alternatively be a sequence of still images. The image data can be in a video or photo format typically used in digital imaging. Examples of such formats include MPEG, AVI, JPEG, H.26X standards, MOV, AVS, WMV, RAW, etc.

A biometric detection engine 102 can receive the image data from the sensor 101, and carry out a detection analysis by the biometric detection engine 102 to detect a biometric signal from the received images, and a biometric parameter associated with the biometric signal. To do so, the biometric detection engine 102 can be configured to calculate an average of the red, green and blue (RGB) values of every pixel in images continuously taken from the cell phone camera's stream, calculated at a suitable frame rate per second, such as 20 Hz or other frame rates. Each calculated RGB average can be considered a sample.

A buffer of calculated averages can be stored in the device as historical samples. The biometric detection engine 102 performs an analysis of the stored averages to determine changes in the RGB average values of the images captured by the camera. In the example illustrated in FIG. 1, the blood flow in the finger with each pulse causes a change in the RGB average value of the image captured by the camera. The changes in the RGB values can be caused, for example, due to the changes in light reflected from a person's skin at different points of the cardiac cycle. In another example, the changes in RGB values can be caused by changes in the shape of the skin due to the expansion and compression of blood vessels at different points of the cardiac cycle.

The biometric detection engine 102 can then apply a statistical autocorrelation to the stored historical samples to determine a periodicity of the changes. The detected periodicity can be interpreted as the biometric signal, which can contain biometric parameters (e.g, heart rate, etc.). For example, the historical samples can be the last 64 calculated averages.

In one example, the autocorrelation functions can be employed via existing hardware present in cellular phones or other computing devices that offer native Fast Fourier Transform (FFT) functions. The autocorrelation analysis can be performed using the Wiener-Khinchin theorem, by which the autocorrelation is computed from the raw data X(t) by applying a Fast Fourier transform (FFT), multiplying the resultant complex vector by its complex conjugate, and finally applying the inverse Fast Fourier transform (iFFT).

The result of the analysis can then be searched for a higher autocorrelation value contained between the $i^{th}$ and the $j^{th}$ index. In embodiments that focus on cardiovascular data, i=(60/M)*S and j=(60/m)*S where m=40 (a minimum beats-per-minute (BPM) boundary), M=160 (a maximum BPM boundary), S=20 (the sampling frequency). In this case, the FFT uses an input size power of 2, so that the number of samples is large enough to contain at least 2 full periods of the heart rate at minimum BPM.

In order to be able to quickly detect changes in heart rate, the biometric detection engine 102 can be programmed to conduct the detection analysis as often as possible. This can be performed by keeping the sample size as small as possible that remains statistically significant. In this example, the sample size can be set to 64, with a sampling frequency of 20 Hz. This allows for an analysis on 3 seconds of samples, which is 2 periods of the minimum BPM, while limiting a delay in reacting to variations of the heart rate to only 3 seconds.

The sampling frequency can also be set high enough to allow the detection engine 102 to detect any sudden changes in the average RGB values during the systolic phase. Testing has indicated that 20 Hz can be a sufficiently high frequency. Other sampling frequencies are also contemplated. The sampling frequency, for example, can be set according to a balance between a desired level of precision in detection analysis and available technical resources (e.g., computational/processing limitations, camera limitations, etc).

Other biometric parameters contained in the biometric signal can then be determined. Power spectral density (PSD) functions can then be employed to derive heart rate variability (HVR) data. From the analysis of the detected heart rate over time the breathing rate can also be derived in the following way: at the end of the inhale phase of a deep breath the heart rate increases from the average value by a noticeable factor (~10%). At the end of the exhale phase the heart rate drops from the average value by another noticeable factor (~10%), and these factors can be correlated to statistically derive a person's breathing rate.

The biometric detection engine 102 can be programmed to perform error correction functions related to the image gathering and detection processes. In an example, a calculated RGB average sample exceeding certain sample thresholds can be filtered out from the sample set used to calculate a heart rate so that a single outlying sample does not corrupt the calculated heart rate.

The detection engine 102 can store a history of filtered samples, and use statistical analysis to determine an image quality value.

The image quality value can be based on one or more of the filtered samples as a percentage of the sample set, the frequency of filtered samples within a sample set, and the number, frequency or pattern of filtered samples across multiple sample sets. For example, reaching or exceeding a certain percentage of individual samples filtered from a sample set or from multiple sample sets can be indicative of a problem with the image capture, such as the user not holding the camera at an appropriate distance from the skin, movement of the camera, poor environmental conditions (e.g. lighting, backlighting, etc.), a dirty lens, etc.

In another example, the biometric detection engine 102 can be programmed to determine that an error has occurred if the calculated RGB averages over time do not change sufficiently to perform the detection analysis. In this example, a minimal threshold change in RGB average can be set over a sample set, over multiple sample sets, over a sampling period. This can be indicative, for example, of image gathering problems such as the camera being too far from the skin to cause RGB value changes in the captured images, or that the camera is positioned over an incorrect or unusable part of the body for this purpose. The image quality value can be based on the determination that the stream of images does not contain detectable differences with which to conduct the detection analysis.

The biometric detection engine 102 can be used to modify the image capture settings of the image sensor 101 to maximize the quality of the image data captured for the functions performed by the biometric detection engine 102.

In one example, the biometric detection engine 102 can conduct initialization detection analysis procedures by running the detection analysis for a defined amount of time (for example, enough for two periods of minimum BPM) for each of several different image capture configurations (e.g., pre-defined "default" configurations, last-used configurations, etc.). An image capture configuration can be considered a collection of or combination of image sensor settings that can influence the image captured by the camera. The settings of the camera can include settings such as aperture, exposure, focus settings, white balancing, contrast, color settings, color filters, flash settings (e.g., timing, brightness, on or off, etc.), resolution settings, frame rate, image stabilization functions, image data format, image data size, etc. The first image capture configuration used in the initialization process can be a "default" capture configuration, such as a current configuration of the camera or a camera's own default configuration. Subsequent image capture configurations can have changes in one or more of the camera settings that result in a different image being captured by the camera. After running the detection analysis for each of the image capture configurations used, the biometric detection engine 102 can select the image capture configuration that results in the best images for the purposes of detection analysis. The number of different image capture configurations tested can be set according to a desired balance of initialization time versus optimizing the image capture configuration.

The initialization detection analysis procedures can be used to customize the detection analysis for an individual user. The initialization detection analysis can determine the optimal image capture configuration for the user's body according to a user's unique skin properties, such as skin color, pigmentation, tone, hair, scarring, etc. The image capture configuration for an individual user can be stored in a user's profile as user configurations, and used in future detection analysis sessions. This facilitates a rapid initialization of the system for that user. Multiple user configurations can be created for a user, such as for images captured at different parts of the body where the person's skin properties might vary.

The user configuration for a particular user can be a global configuration (i.e., it is obtained when the user first uses the system then saved), can be session configuration (i.e., calculated from scratch every time the user uses accesses the system), or can be a combination of the two (e.g., a global configuration that can evolve over time to account for changes in the appearance of the user, a global configuration whose settings can be changed for that session only to account for single-session or short-term changes in the appearance of the user or instant environmental conditions, etc.).

In an embodiment, the image can be separated into three images, each image corresponding to the red, green and blue values of pixels in the image, respectively. For each of the red, green and blue images, the average values can then be calculated as discussed above, and the analysis performed to detect a biometric signal for each. The biometric detection engine 102 can then evaluate a detection strength based on the detection results for each of the red, green and blue images to determine their individual effectiveness within the detection analysis. This separation of the image and analysis of each separated image can be performed as part of the initialization detection analysis procedures.

The biometric detection engine 102 can then conduct the detection analysis for the purposes of generating the biometric data by continuing the detection analysis using the "strongest" of the red, green and blue images. The biometric detection engine 102 can perform detection analysis on the other two colors individually or in combination for error checking, or to check whether changes in the captured images have changed the "strongest" color (such as because of changes in environmental conditions, camera settings, etc.). The detection analysis of the remaining colors can be performed at a different sampling rate than the strongest color, such as at a lower sampling rate. After the selection of the color to be used in detection analysis, the detection engine 102 can generate a color selection identifier containing information related to the color selection. For example, the color selection identifier can include identification of the current strongest color, as well as data related to the strength of the selected colors and the remaining colors. Some or all of the information included in the color selection identifier can be integrated into one or more of the image capture configuration and the detection quality value.

In another embodiment, the detection engine 102 can separate the images into the red, green and blue images as described above. The detection engine 102 can then assign weights to each of the red, green and blue values according to their relative strengths. Thus, the calculated average of the RGB value as described above is calculated according to the weighted values of the individual red, green and blue values. As such, the calculated average of the RGB value emphasizes the "strongest" color. The detection engine 102 can generate RGB weight data based on the calculated average that can be incorporated into one or more of the image capture configuration and the detection quality value.

The system includes a music generation engine 103 configured to transform the biometric data into one or more musical structures. In an embodiment, the music generation engine 103 can use a moving average of the heart pulse in order to derive a beats-per-minute calculation. The beats-per-minute can be used as an internal clock, acting as a global metronome. The global metronome can be subdivided into measures, bars, beats or ticks. The music generation engine 103 can be a procedural content generation engine (PCG).

Figure 2:
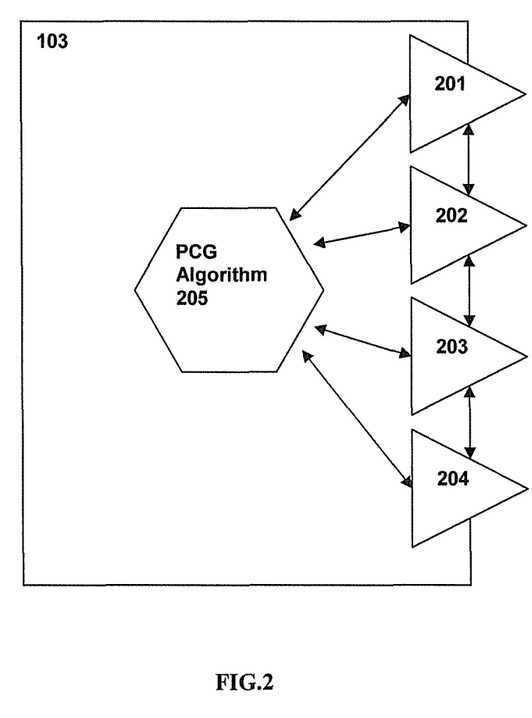
FIG. 2 is an overview of the modules of a music generation engine, according to an embodiment of the inventive subject matter.

In an embodiment, the music generation engine 103 can include various modular components configured to handle specific aspects of the music signal generation. FIG. 2 illustrates an example, wherein the generation engine 103 can include a rhythmic module 201 configured to generate rhythmic content, a melodic module 202 configured to generate melodic content, a genetic content generation module 203 configured to generate genetic content (e.g., content unique to the user, based on user configurations, etc.), and a quality module 204 configured to generate quality content. Each of the modules 201,202,203,204 can be in communication with all of the other modules, permitting the exchange of data, instructions, and allowing for the cooperation between the modules in completing content generation functions.

In one example, the system can make use of the Pure Data (Pd) dataflow system written by Miller Puckette and others, licensed under the terms of the Standard Improved BSD License. A parallel project of Pure Data, libpd# (also under BSD license) can be used within the system to build the PCG that can be embedded into mobile operating systems, such as iOS and Android mobile operating systems.

Examples of music generation algorithms include the artificial intelligence techniques developed by Davide Morelli and David Plans, and described in academic papers (2007, 2008) and David Plans' PhD Thesis, entitled "Remembering the future: genetic co-evolution and MPEG7 matching used in creating artificial music improvisers.", submitted to the University of East Anglia in the UK in July 2008. Procedural generation of musical content in a similar application is also described by the authors in an upcoming IEEE Journal paper (see David Plans and Davide Morelli, "Experience-Driven Procedural Music Generation for Games", IEEE Transactions on Computational Intelligence and AI in Games, special issue: Computational Aesthetics in Games, June 2102).

In an embodiment, the music generation engine 103 can generate a music signal by using the biometric parameters (e.g., heart rate, breath rate, pulse, HRV, etc.), the image quality value and the user's profile, to identify one or more music features.

The music features can be considered the building blocks of the music signal. Examples of music features include rhythm features, melody features, tone features, scale features, tempo features, note features, pitch features, instrument sound features, phrase impulse features, harmony features, beat features, metronome features, timing features, sound sample features, key features, musical progression features, etc. The music features can be embodied as instruction sets, rule sets, data sets, data objects, templates, etc. The music features can be stored in a music database 105 that can be accessed by the music generation engine 103 during the music generation process. The music database 105 can be local to the music generation engine 103 (i.e, stored in the memory of the device housing the music generation engine 103), a database in a remote server accessible by the music generation engine 103 via a network connection, or a combination thereof. Music features can be associated with other music features. For example, certain melody features and/or tempo features can be associated with rhythm features that correspond to particular rhythms to which certain melodies and tempos are well suited.

Music features can also include modifiers that change or modify other music features. For example, a music feature can be a rhythm modifier for a rhythm music feature, which can be used to modify the rhythm aspect of the music signal. In another example, a modifier can be used to emphasize or de-emphasize certain notes, instruments, to change keys, to modify the tempo, etc. Modifiers can be used to modify or change music features prior to the generation of the music signal. Alternatively, modifiers can be used to modify a music signal after it has been generated.

Music features can further include quality modifier features. Quality modifier features can be used to affect music signal such that the quality of the music experienced by the user is changed. The quality modifier features can be features that actively modify the generated music signal quality or features that simulate a change in music signal quality. For example, a quality modifier that actively modifies the generated music signal can be a feature that amplifies some or all of the music features used in generating a music signal, or of the generated music signal itself. An example of a simulating modifier feature can include a feature that adds audible noise to the music signal. Quality modifier features can include quality reduction features that degrade or reduce the quality of the music output. Examples of music quality reduction features include interference features (i.e., features that interfere with the music signal or the output music), a speaker feedback feature (i.e., noise sounding like speaker feedback to the music signal), a radio static feature (i.e., noise sounding like radio static, such as when a radio is picking up a weak or no signal), a low volume feature (i.e., reduces the volume of the output), a disk skipping feature (i.e., noise that sounds like a skipping compact disc or record), a cassette failure feature (i.e., noise that sounds like a cassette malfunction), a stereo output feature (i.e., can alter the music signal so that the output sound is heard in monaural instead of the default stereo), a speaker failure feature (i.e., the music signal is modified so that the output music sounds like it is being played through a blown or otherwise defective speaker), an echo feature (adding an echo to the audio output), a crowd boo feature (i.e., sounds like a crowd booing at a live event such as a concert or a sporting event), and a noise feature (e.g., random yelling, unpleasant environmental sounds such as construction or traffic noises, etc).

To generate the music signal, the music generation engine 103 can first perform a mapping of the biometric parameters derived from the biometric signal with music features. The mapping can be performed according a variety of mapping techniques and mapping rules. For example, the mapping can be performed based on pre-determined relationships between biometric signals and music features. Examples of mapping techniques include one-to-one matching, one-to-many matching, many-to-one matching, statistical analysis, clustering analysis, etc. In an embodiment, the music generation engine 103 can construct content layers corresponding to the different characteristics of a musical composition. The music signal is then generated based on the content layers, such as by a combination of the content layers or by a sequential, hierarchical relationship. For example, the music generation engine 103 can generate rhythmic content, melodic content, genetic content, and quality content.

In one illustrative example, the music generation engine 103 can use the biometric parameter corresponding to the heart beat in beats-per-minute (BPM) can correlate to metronome features, which can be used to generate a global metronome as a foundation for the music signal. In an embodiment, the BPM calculation can be derived from a moving average of the heart pulse. The metronome features can include subdivision or marker data that allow the generated global metronome to be sub-divided into measures, bars, beats or ticks. In embodiments, this global metronome can then be used as a baseline for the modular components that instrument the real-time, automatic music generation algorithm.

The rhythmic characteristics of a generated musical composition can be thought of as the rhythmic content of the music signal. The rhythmic content can be generated by synchronizing rhythmic music features with the global metronome. The rhythmic features used in the generation of the music signal can also be directly associated with bands of cardiovascular parameters or other periodic biometric parameters. In an example, a heart rate in BPM can be subdivided into bands of 45-65, 65-75, 75-90, 90-110 and higher than 110 BPM. A heart rate parameter falling into a particular band can correspond to rhythmic features associated with that band, and a change in band will result in a change in rhythmic features used to generate the music signal. As such, the rhythmic structure of the music signal can be dynamically adjusted according to changing biometric conditions. The rhythmic features used can include rhythm features (e.g, metric levels, rhythm units, etc), beat features, and other music features that can affect the rhythm of a musical composition. Music features used in the generation of rhythmic content can also include sound features and instrument features, such as those typically associated with rhythm in music. Examples of this kind of music feature can include synthesized sounds and/or sampled drum audio, bass sounds, etc.

The generation of the rhythmic content can be performed by a rhythmic module 201. The rhythmic module 201 can include procedural music generation algorithms that can synch music features to the global metronome. The generation of rhythmic content can respond directly to the bands of cardiovascular data or other periodic biometric data described above. Each band can include trigger messages that instruct the rhythm module to adjust the rhythm. The rhythm adjustment can be achieved by retrieving new music features that synchronize with the current band (and global metronome), or by modifying the existing music features according to the current band BPM average.

The melodic characteristics of a music composition can similarly be thought of as the melodic content of the music signal. Examples of the musical features used in the generation of the melodic content can include phrase impulse features (i.e., a series of notes of a certain length), melody features, pitch features, note features, tone features, key features, tempo features, harmony features, scale features, progression features, etc. Scale features can include features associated with scale degrees, such as major (Ionian), minor (Aeolian), Phrygian, Lydian and whole tone. Sound and instrument features typically associated with melody can also be associated with the melodic content. Examples of this type of music feature can include synthesized and/or sampled voice audio, instrument audio, etc. The music features used in generating melodic content can be associated with biometric parameters directly, including the some or all of the same biometric parameters used in the generation of the rhythm units. A selected music feature can also be indirectly associated with biometric parameters, wherein the music feature is selected based on its associations with another selected music feature that is directly associated with a biometric parameter. Music features used in generating melodic content can also be selected based on the rhythmic content (by way of the global metronome).

The melodic content can be generated by the melodic module 202. The melodic module 202 can include content generation algorithms to procedurally generate melodic content. The melodic module 202 can be in communication with the rhythmic module 201. As such, the melodic module 202 can exchange messages from the rhythmic module 201 (by way of the global metronome) that trigger the incorporation of musical features, such as phrase impulses, and to ascertain the global tempo. The global tempo can be ascertained via tempo features, algorithmically, or a combination thereof. As such, biometric signals are translated into melodic content via their corresponding music features. The melodic module 202 can further include a concept of scale degrees based on scale features, such as those described above.

User profile information can also be employed in the music signal generation process. One or more aspects of the user profile information can be mapped to music features, which are then included in the generation process, allowing for the customization of the generated music signal to the individual user. The music features used can be additional music features from the same pool used to map biometric parameters and/or modifier features used to modify selected music features as described above. The mapping of music features with user profile information can be performed using the techniques described above.

In an embodiment, the individual user configurations within a user profile can each correspond (and be mapped to) to different music features that are incorporated into the music generation process. As such, the music signal generated will be unique to the user, and also unique to the conditions in which a particular user configuration is used for image capture. For example, if a user has multiple user configurations corresponding to different parts of the body, the music generated by capturing image data of the user's finger will be different than the music generated by capturing image data of the user's face. Over time the user can form associations of music signals having a particular modified sound with the body part that causes the particular modification. This association can provide the user with a degree of freedom to select how the music signal is generated that is also directly encouraging a user to optimize their participation in the image capture process.

In an embodiment, the music (and/or modifier) features corresponding to user profile information (such as the user configurations) can be used to create the genetic content of a music signal. The genetic content can be the collection of music and/or modifier features associated with the user profile information, or can be created as a function of these features. The genetic content can also be created using the user profile data either by itself or in combination with associated music/modifier features.

The genetic content of the music signal can be generated by a genetic content generation module 203. In an embodiment, the music and/or modifier features of the genetic content can be used to modify certain aspects of the music signal, such as certain music features implemented in the rhythmic and melodic contents. In another embodiment, the genetic content can be used to modify the rhythmic and/or melodic content as a whole. The genetic content generation module 203 can include procedural generation algorithms (such as those implemented by Morelli and Plans discussed above) that can generate unique genetic content.

In an embodiment, the user profile and/or the features can be used as seed elements for the generation of the genetic content by the genetic content generation module 203. For example, the user configuration can be used as a seed to generate the genetic content, which will modify the music signal and thus change the music audio heard by the user. Using a different user configuration will result in a different genetic content and thus, a different music signal. Other seed values can be used in addition to the user profile data, such as cell phone device ID, telephone number, MAC address, IP address, HVR signature, location information (e.g., GPS, triangulation, etc.), and health status information. The seed values can be hashed values, such as a one-way hash function string.

The music generation engine 103 can also incorporate quality modifier features into the music signal. The quality modifier features can be selected by the music generation engine 103 based on the image quality value reflecting the quality of the captured image data. Image quality values can be mapped, such as via the techniques described above, to one or more corresponding quality modifier features. The association between image quality values and quality modifier features can be based on one or more factors such as the technique used to derive image quality values, the image capture factors affecting the image quality values, etc. Additionally, the image quality value can include information indicating an intensity of the corresponding quality modifier feature, which can be used to control the degree to which a quality modifier feature will affect a music signal. This intensity information can be, for example, associated with a magnitude of the image quality value, or the image quality value meeting or exceeding certain thresholds, tolerances, ranges, etc.

In an illustrative example, the image quality value can correspond to a quality modifier feature that introduces an effect simulating radio static to the music signal, with the intensity of the effect proportional to the level of captured image data quality as represented by the image quality value. In this example, an image quality value reflecting captured image data having a high quality (e.g., having an acceptable number of errors, etc.) can result in no static effect being added. As the quality of the captured image data deteriorates (such as by the user moving the image sensor too close or too far away from the body part), the static effect can be increased. If the image data received is of such low quality so as to be nearly or completely unusable, the static effect can be made to completely drown out any other audio. This use of a quality modifier feature can be used by the system to direct the user to correct low-quality image capture, such as by changing the position of the image sensor relative to the captured body part to result in music with "better reception" via reduced (and ultimately eliminated) "radio static". The modification of the music signal via a quality modifier further allows the system to direct the user into performing corrections via audio cues, such that the user can make the corrections in image capture situations where the body part being captured does not permit the user to see the device's screen.

A sudden change of image quality value (e.g., a change in image quality value exceeding a certain magnitude) can be associated with a quality modifier value. For example, a sudden drop in image quality value (e.g., a change in image quality exceeding an acceptable magnitude occurring within a certain time) can be associated with a quality modifier value that introduces an audio effect of a record or disk skipping into the music signal. In cases where the drop in image quality is such that the image quality values calculated after the sudden remain below a threshold (i.e., indicative of unusable captured image data), the skipping effect can be repeated until the image quality value return to acceptable levels. As such, these quality modifier values can be used to provide an indication of the occurrence of single, sudden events (such as a sudden movement of the image sensor or temporary loss of focus) that can also serve as a reminder to the user to keep the image sensor sufficiently still to be capable of capturing usable image data. Similarly, these quality modifier values can be used by the system to alert the user to an ongoing problem with the image capture and direct the user to take action, such as an alert that the placement of the image sensor relative to the body part in the image sensor being obscured resulting in the user moving the image sensor away from the body part.

The quality modifier features can be incorporated into the music signal via the creation of quality content. The quality content can be procedurally generated by a quality module 204, and can be a collection of the quality modifier(s) and quality modifier value(s) associated with an image quality value. Where the quality modifier features involve an interruption of the music signal output (such as in the "disc skipping" example illustrated above), the quality module 204 can transmit a message to the other modules instructing them to adjust their respective content generation to account for the interruption, or to wait until further instruction to resume (such as for extended interruptions).

The music generation engine 103 can be configured to incorporate externally generated audio samples (such as studio-generated music tracks) into the music signal by syncing the sample to the global metronome. To enable this function, the music generation engine 103 can incorporate sample media players such as players having Pure Data components.

The generated music signal can be provided to a media player 104 to produce audio signals according to the music signal, such as music. To do so, the music generation engine 103 can export the music signal to the media player 104. As needed, the music generation engine 103 can also provide instructions, applications, or other code to enable the music player 104 to convert the music signal into audio signals.

The music signal can be generated in a various formats that allow for the conversion of the music signal into audio output. Examples of music signals can include a collection of tracks combinable to form the music (such as via music editing programs), a generated music data file in standard or commonly-used digital audio formats (e.g., MIDI, MP3, WAV, streaming music, etc.), electrical audio input signals used to generate music in a speaker, etc.

In modular embodiments, the music generation engine 103 can include one or more procedural content generation algorithm 205 in addition to, or instead of, the individual procedural content generation algorithms belonging to the modules. In an embodiment, the additional algorithms 205 can perform content generation for modules lacking native procedural content generation algorithms, based on generation instructions from these modules (e.g., what music features to for that particular content, when to switch features, etc.). In another embodiment, the additional algorithms 205 can perform the function of combining the separate content items from their respective modules into a finalized music signal.

In an embodiment, the music generation engine 103 can be entirely contained within a cellular telephone device or other suitable computing device. As such, the procedural content generation engages the user at a device-oriented point of interaction. In alternative embodiments, the music generation engine 103 can be distributed across multiple devices networked together, or can reside entirely in a remote device such as a server.

The system can further include server applications, such as applications allowing users to sync data from their mobile devices to a web application.

The server applications can include the storage of user profiles in a user database 106 stored on one or more remote servers accessible via the user client devices. The servers can also include the music feature database 105. Generated music signals can also be stored on the servers, allowing for a user to retrieve previously generated music signals to listen to again, or to share with other users.

User data can be obtained via one or more JSON functions within system application developer packages. For example, heart rate variability can be obtained and then sent to a server application.

The server application can be written in Node.js (a JavaScript web framework) and configured to accept JSON requests and store these requests in a custom database, such as those contained in a MongoDB instance. The client-server system architecture enables various server-side services, such as push-based health information. For example, the user can receive information regarding the user's level of stress, derived from HRV data on a particular point of his/her week.

The database can be configured to store information on user data from each mobile session. Further, the database can be designed to store other relevant information such as unique keys and usage data.

An analysis server can utilize one or more algorithms to analyze user data using data mining techniques for timed series. Segmentation algorithms such as "Sliding Windows" or "SWAB" and "Piecewise Linear Representation" allow for removing noise of measurements and split data into segments with similar features (flatness, linearity, monotonic, etc.). Pattern detection, clustering and classification will then be performed to detect periodicity and outliers in trends. Algorithms like Artificial Neural Networks, Self Organizing Maps, Support Vector Machines or Bayesian classifier can be used to classify, detect patterns and assign indirect measures to segments. Additional techniques can be performed including Principal Component Analysis (PCA) or K-means to reduce the dimensionality of the data, and to look for meaningful patterns and periodicity. The analysis server can apply these techniques to collected user data and forecast events (such as stress peaks) before they happen. The forecasted events can be communicated to the user and viewed on their device. The analysis and forecasting can be performed by a health inference engine within the analysis server, and the user data used in forecasting can be the generated music signal, the raw biometric signal derived from the image data, or a combination of the two.

In an embodiment, a forecasted event can have associated music features, and can be used to modify a generated music signal. To do so, the server can communicate the event as well as associated music generation data (e.g., music features, seed values, etc.) to the music generation engine 103. The forecasted event can then be integrated into the music generation process, such as by integrating the forecasted event data into the genetic content generation. The nature of the music features associated with a particular forecasted event (and consequently, the effect the music features will have on the generated music signal) can be related to factors such as the immediacy of the forecasted event, the severity of the forecasted event, the likelihood the forecasted event will occur, and the risk the forecasted event presents to a user. In an embodiment, an explanation of reason behind the modification of the music can be provided to the user as well, so that the user can be aware of the forecasted event.

In another aspect, the present invention contemplates that biometric data can be collected and aggregated across a crowd, an audience for example. Further, as discussed below, the aggregated biometric data can be converted to a multimodal presentation for consumption by a stakeholder. Thus, within the context of live entrainment, the disclosed system can offer a live environment that allows the audience or performer to interact in unprecedented ways. As such, one will appreciate that the disclosed techniques provide for aggregation of biometric information and transforming the biometric information to a set of multimedia presentation signals that command a device to present a multimedia presentation.

In one embodiment, the invention provides a biometric data processing system including: a) a biometric interface configured to acquire biometric data sets from distinct biometric sensor platforms, each biometric data set corresponding to an individual; and b) a biometric processing engine coupled with the biometric interface and configured to: obtain the biometric data sets; derive a group biometric state as a function of the biometric data sets; generate a media presentation based on the group biometric state; and configure a presentation computing system to render the media presentation. The system is adapted to include a plurality of smart phones configured to operate as the biometric sensors. Additionally, the group biometric state may include an average biometric, such as one or more of a heart rate, a breath rate, a galvanic value, a movement, a tension, a stress level, a perfusion, an airway patency, and a blood pressure.

Figure 3:
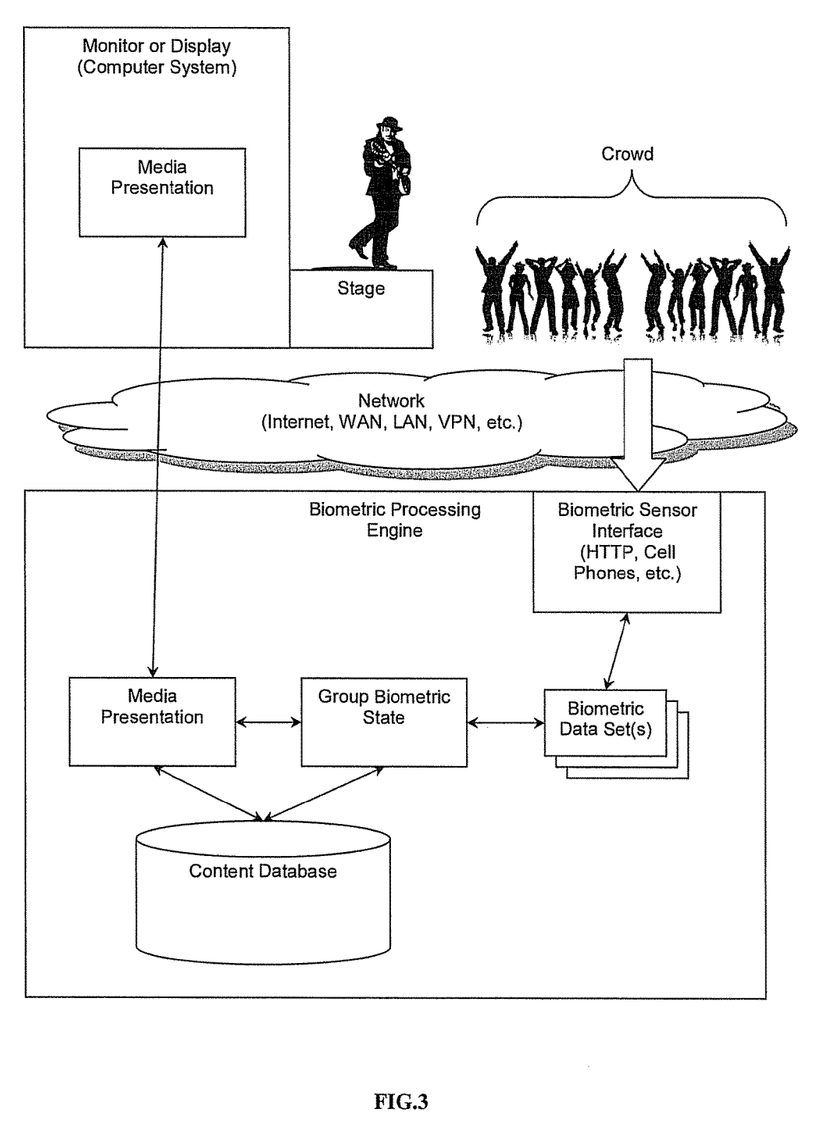
FIG. 3 is a schematic of a biometric processing system capable of generating a media presentation as a function of a group biometric state, according to an embodiment of the inventive subject matter.

FIG. 3 presents an overview of a crowd-based biometric acquisition system within the context of a live performance. One should appreciate that the venue could also include a game, a sporting event, a movie, a play, a concert, an on-line video gaming event, a television show, or other environment in which multiple individuals can participate as a group or a crowd.

In some embodiments, members of the crowd have mobile device, their cell phones for example, configured as biometric acquisition systems that collect biometric data sets of the individuals. Example techniques for configuring a cell phone to collect biometric data include those discussed herein. The biometric data sets can be acquired via a biometric interface (e.g., the crowd's cell phones, an HTTP server, etc).

A biometric processing engine collects or otherwise obtains the biometric data sets, for example over a network (e.g., cell network, internet, peer-to-peer network, WAN, LAN, PAN, etc.). The engine leverages the data sets to derive a group biometric state reflecting the biometric status of the group of a whole. For example, in the context of a live performance, the group biometric state might include a trend in an average heart rate across the crowd. The group biometric state can include statistical information reflecting the aggregation of data across the biometric data sets including heart rate data, breathing rate data, derive stress levels, group movement (e.g., based on geolocation information, accelerometry, video tracking, etc.), synchronized behaviors (e.g., jumping or dancing to the beat of a song), or other types of data. Each attribute value (e.g., heart rate) of the group biometric state could be multi-valued where the corresponding attribute value could include an average and a range (e.g., statistical spread, minimum, maximum, etc.).

The processing engine generates one or more media presentations based on the group biometric state where the media presentation could include visualization elements, sonified elements, graphic data, animations, video, or other types of content. Thus, the performer, venue owner, audience, crowd, or other stakeholder can observe the group state as well as interact with the media presentation. One should keep in mind that any stakeholder (e.g., performer, venue owner, etc.) could also be considered a member of the crowd. For example, a performer on stage could observe that the group heart rate is trending up based on the visual or sonified information within the media presentation. Based on the information, the performance could play a slower song in an attempt to lower the heart rate of the crowd, or even play a faster song to increase the rate at which the group's collective heart rate is trending up.

The media presentation can include any type of content modality including, but in no way limited to image data, video data, computer generated graphics, real-time graphics, audio data, game data, advertisements, or other types of date. In some embodiments, the content can be obtained from a content database storing desirable types of content. For example, the content could be indexed by biometric state attributes or their values (e.g., heart rate, heart rate value, etc.). Once the processing engine derives an attribute as part of the group biometric state, the engine can query the content database for content or content templates that have been indexed based on such attributes. Thus, the content and biometric attributes can both adhere to a common attribute namespace.

In another aspect, the present invention contemplates use of a photoplethysmograph to derive a physiological or psychological state. Such bio-state information can then be leveraged to construct one or more content lists (e.g., music play lists, videos, etc.) that can be curate to the state. As such, one will appreciate that the disclosed techniques provide for converting biometric data into a bio-state, which in turn can be used to generate signals that configure a device to present content related to the bio state.

As discussed previously in further detail the present invention provides technology solutions that offer insight into users' cardiovascular health in a comprehensible way that requires no medical knowledge, and that uses no specialist hardware. Rather the techniques leverage ubiquitous devices, such as a mobile phone, gaming device, kiosk, vehicle or other computing device to collect and analyze biometric data to make statistical predictions as to hypertension, levels of stress, or other bio-states.

In one embodiment, the invention provides a method which includes: a) configuring a mobile device to operate as a content management engine; acquiring, by the content management engine, biometric data from the mobile device; deriving, by the content management engine, bio-state of an entity as a function of the biometric data; generating, by the content management engine, a content list from the bio-state; and configuring the mobile device to render content associated with the content list. In various embodiments, the bio-state may be by a physiological state or a psychological state. The step of generating the content list may further include classifying content according to an ontological classification scheme according to bio-state attributes representative of the bio-state, such as, but not limited to one or more of stress levels, endurance levels, galvanic response, emotional characteristics, and vocal tone. Further, the content list may include one or more of the following types of content: image data, audio data, music data, video data, game data, shopping data, medical data, and family data.

Figure 4:
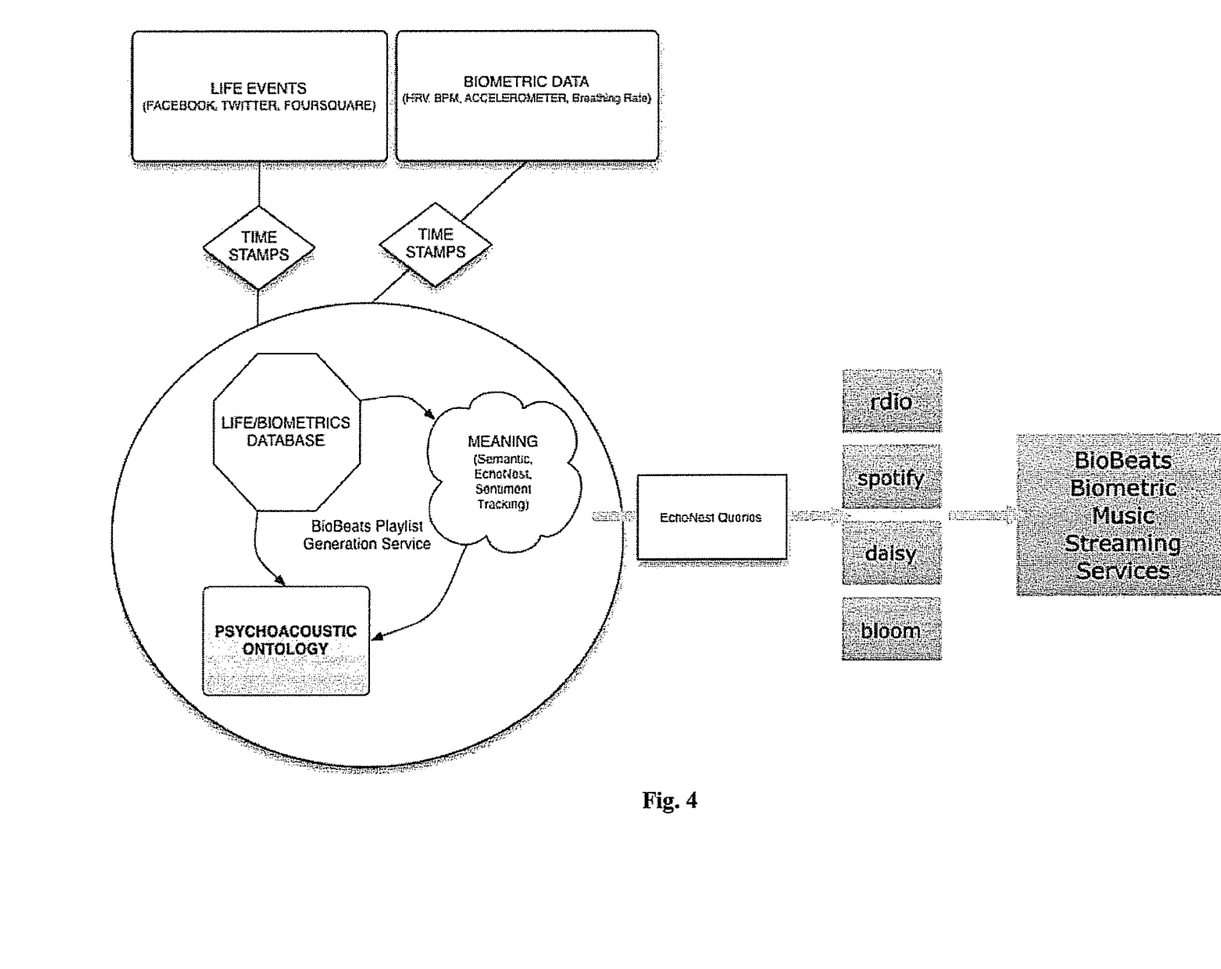
FIG. 4 illustrates a method of generating content lists from a bio-state, according to an embodiment of the inventive subject matter.

With reference to FIG. 4, within the context of content or music discovery and the provision of content streaming services, the disclosed approach uses the photoplethysmograph signal acquired by the methods previously outlined, to determine the subjects' bio-state (e.g., physiological and/or psychological status) in terms of relative bio-state attributes (e.g., stress levels, emotional state, tone of voice, and the like). This data is then filtered through an ontological algorithm that pairs particular levels of stress with particular clusters of content attribute, music timbre for example, (e.g., high frequency content might not pair well with high level of stress) in order to derive a psycho-content correlation between biometric data and particular genres of content. For example, particular paces (Beats Per Minute) or other parameters can be mapped to content features; rhythm, melody, speech patterns, etc. After this relationship is established, the mobile device operating as a content management engine can engage APIs such as the Echo Nest™ to search for music titles, or other content, that match the results of the ontological search. Once results are acquired, the target content can be streamed via services such as, but not limited to RDio™, Spotify™, and Bloom.fm™, to dynamically build playlists that can be returned to the device of the instant invention, e.g., mobile device. This playlists generation engine is advantageously service agnostic and is modularly designed, to be ready for incoming music services such as Beats By Dre's Project Daisy™, that might offer more forward-thinking personalization API points.

In another aspect, the present invention contemplates providing cross-modality feedback (e.g., musical sonification, visual stimuli, etc.) from biometric data to provide therapeutic effects on the user. For example, a device of the present invention, such as a cell phone operating as a photoplethysmograph configured to generate a visualization or audio representation of the user's breath rate, can be utilized to influence physical or mental therapy. As such, one will appreciate that the disclosed techniques provide for observing biometrics of an entity and using corresponding biometric data to generate signals that cause a device to render a therapy to the entity.

In one embodiment, the invention provides a therapy system which may include: a) a biosensor interface configured to acquire biometric data; and b) a therapy engine coupled with the biosensor interface and configured to: obtain the biometric data via the biosensor interface; construct a digital therapy regimen associated with a therapy as a function of the biometric data, the digital therapy regime comprising rendering instructions; and configure a device to render the digital therapy regimen according to the rendering instructions.

Figure 5:
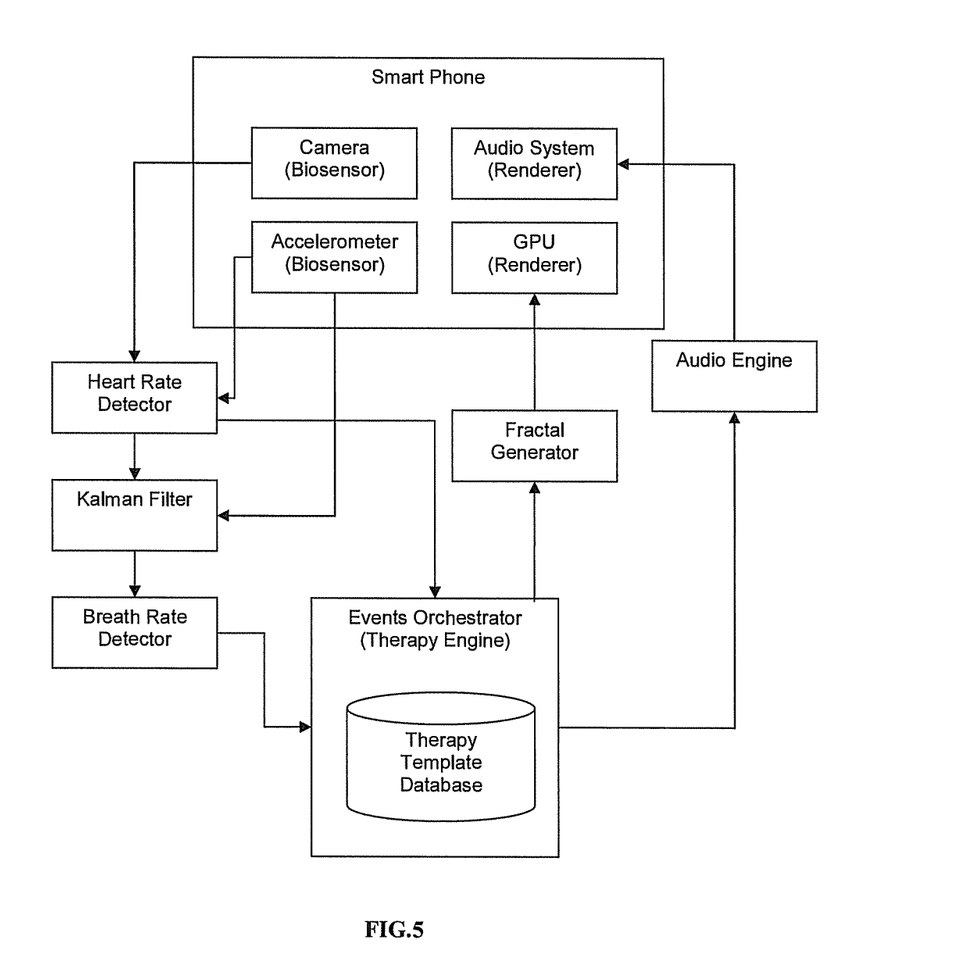
FIG. 5 is a schematic of a therapy system, according to an embodiment of the inventive subject matter.

FIG. 5 illustrates a therapy system in one embodiment of the invention. The system of FIG. 5 is configured to make long-term statistical health predictions such as the onset of atherosclerosis, hypertension, or dangerous levels of stress through observation of biometric device obtained via a sensor interface (e.g., a person's smart phone). In one embodiment, this may be considered in the context of chest physiotherapy or breathing-focused mindfulness-based stress reduction. The system can obtain a photoplethysmograph signal acquired via image data not only to determine the subjects' hemodynamic status, but to also determine breath rate, such as via one or more accelerometry sensors (i.e., acceleration data from the phone's own sensors, movement, etc.). Example techniques that estimate respiratory rate from photoplethysmogram data are described in Chon, K. H., Dash, S., & Ju, K. (2009) titled "Estimation of Respiratory Rate From Photoplethysmogram Data Using Time & Frequency Spectral Estimation" (Biomedical Engineering, IEEE Transactions on. doi:10.1109/TBME.2009.2019766).

Upon deriving an estimated respiratory rate, or other biometric data, the biometric data can be mapped to one or more therapy regimens that could include multimodal outputs including visualizing or sonifying aspects of human breath. In various embodiments, the digital therapy regimen includes instructions to generate at least one of the following modalities of data: audio data, image data, video data, haptic data, kinesthetic data, olfactory data, and taste data.

Such biometric data information, as discussed above, can be derived from either or both an accelerometry or photoplethysmographic perspective. In various embodiments the biometric data that is collected may include at least one of the following: a breath rate, image data, audio data, accelerometer data, pulse oximetry data, EKG data, EEG data, galvanic data, and temperature data. In one example, data from a photoplethysmograph signal, acquired from a mobile phone's camera, and from the movement signal, acquired from a mobile phone's accelerometer/gyroscope, provide sonification and visualization feedback, in order to achieve particular chest therapy and mindfulness therapy techniques, in particular Active Cycle Breathing and Pranic (Pranayama) Breathing exercises.

In one embodiment, the invention provides a system as outlined in FIG. 5 which includes the following components:

Biosensor Interface: A smart phone as a sensor platform, for example

Captures image data, acceleration data, audio data, etc.

Derive breathing rate from acceleration data via frequency or periodicity in acceleration Derive photoplethysmographic data by sampling frequency of changes in video data with respect to one or more color channels (e.g., green).

Heart Rate Detector (possibly in therapy engine): Derive heart rate based on R-R peak detector algorithm Kalman filter (possibly in therapy engine): Enhance heart rate signal using correlated accelerometer signal, filtering out noise from movement Breath Rate Detect (possibly in therapy engine): Map accelerometry data to a breath rate Events Orchestrator (therapy engine): Use biometric data to trigger events to construct therapy regimen having render instructions Audio Engine (smart phone, user device): Present audio modality according to rendering instructions via device's audio system Fractals Generator: Generate images or graphics according to rendering instructions GPU: Configure device to render visual therapy according to graphic rendering instructions It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Although the present process has been described with reference to specific details of certain embodiments thereof in the above examples, it will be understood that modifications and variations are encompassed within the spirit and scope of the invention. Accordingly, the invention is limited only by the following claims.

What is claimed is:

1. A therapy system comprising:
   a biosensor interface configured to acquire biometric data, the biosensor interface comprising an image sensor configured to capture image data, wherein a biometric signal is derived from the captured image data and one or more biometric parameters associated with the biometric signal are extracted therefrom; wherein further the image data captured by the image sensor is separable into red, green and blue images weighted according to the strength of detection of the biometric signal, wherein the biosensor interface is configured to perform a detection analysis on a selected color at a higher sampling rate than said other colors; and wherein the biosensor interface is configured to generate a color selection identifier containing information relating to said selected color for a user, said color selection identifier being integrated into an image capture configuration; and
   a therapy engine coupled with the biosensor interface and configured to:
      obtain the biometric data via the biosensor interface;
      construct a multimodal digital therapy regimen associated with a therapy as a function of the biometric data, the multimodal digital therapy regimen comprising rendering instructions to generate a visual or audio signal, wherein the generated visual or audio signal provides a visualization or audio representation of one or more aspects of the biometric data; and
      configure a device to render the multimodal digital therapy regimen according to the rendering instructions,
      the therapy engine further comprising a therapy template database configured to store template objects representing the therapy, wherein the therapy engine is further configured to identify at least two of the template objects based on the biometric data and incorporate the identified at least two template objects into said generated visual or audio signal to provide the visualization or audio representation of one or more aspects of the biometric data; and
      a communication interface to communicate the multimodal digital therapy regimen as a media presentation to a user of the system.

2. The system of claim 1, wherein the multimodal digital therapy regimen is associated with a chest therapy.

3. The system of claim 1, wherein the multimodal digital therapy regimen is associated with a mindfulness therapy.

4. The system of claim 1, wherein the multimodal digital therapy regimen is constructed based on an active cycle breathing exercise template.

5. The system of claim 1, wherein the multimodal digital therapy regimen is constructed based on a pranic breathing exercise template.

6. The system of claim 1, wherein the biosensor interface comprises a photoplethysmograph.

7. The system of claim 6, wherein the photoplethysmograph comprises a smart phone.

8. The system of claim 1, wherein the biosensor interface comprises a smart phone.

9. The system of claim 1, wherein the therapy engine comprises a mobile computing device configured to operate as the therapy engine.

10. The system of claim 9, wherein the mobile computing device comprises at least one of the following: a cell phone, a media player, a medical device, a vehicle, a tablet, a phablet, and a game device.

11. The system of claim 9, wherein the therapy engine comprises a remote server configured to operate as the therapy engine.

12. The system of claim 9, wherein the multimodal digital therapy regimen comprises instructions to generate at least one of the following modalities of data: audio data, image data, video data, haptic data, kinesthetic data, olfactory data, and taste data.

13. The system of claim 9, wherein therapy engine is further configured to obtain additional biometric data in response to a previously rendered therapy regimen.

14. The system of claim 9, wherein the biometric data comprises at least one of the following: a breath rate, image data, audio data, accelerometer data, pulse oximetry data, EKG data, EEG data, galvanic data, and temperature data.

15. The system of claim 1, wherein all of the elements of the system are physically present in a single device.

16. The system according to claim 1, wherein the biometric interface is configured to perform detection analysis on a strongest color at said higher sampling rate than said other colors.

17. The system according to claim 1, wherein the biometric interface is configured to store weightings of the red, green and blue images as a weighted proportion between the red, green and blue images for an individual user.

18. A therapy system comprising:
    a biosensor interface configured to acquire biometric data, the biosensor interface comprising an image sensor configured to capture image data, wherein a biometric signal is derived from the captured image data and one or more biometric parameters associated with the biosensor signal are extracted therefrom; wherein further the image data captured by the image sensor is separable into red, green and blue images weighted according to the strength of detection of the biometric signal; and
    a therapy engine coupled with the biosensor interface and configured to:
       obtain the biometric data via the biosensor interface;
       construct a multimodal digital therapy regimen associated with a therapy as a function of the biometric data, the multimodal digital therapy regimen comprising rendering instructions to generate a visual or audio signal, wherein the generated visual or audio signal provides a visualization or audio representation of one or more aspects of the biometric data; and
       configure a device to render the multimodal digital therapy regimen according to the rendering instructions,
       the therapy engine further comprising a therapy template database configured to store template objects representing the therapy, wherein the therapy engine is further configured to identify at least two of the template objects based on the biometric data and incorporate the identified at least two template objects into said generated visual or audio signal to provide the visualization or audio representation of one or more aspects of the biometric data; and a communication interface to communicate the multimodal digital therapy regimen as a media presentation to a user of the therapy system, the communication interface being configured to modify a quality of the media presentation based on a detected quality of the images provided by the image sensor, wherein a biometric detection engine determines the detected quality of the images.

\* \* \* \* \*